US006423748B1

(12) United States Patent
Park et al.

(10) Patent No.: US 6,423,748 B1
(45) Date of Patent: Jul. 23, 2002

(54) AMIDO POLYBIGUANIDES AND THE USE THEREOF AS ANTIMICROBIAL AGENTS

(75) Inventors: Joonsup Park; Nathaniel D. McQueen, both of Arlington, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/646,560

(22) PCT Filed: Dec. 17, 1999

(86) PCT No.: PCT/US99/30207

§ 371 (c)(1),
(2), (4) Date: Sep. 19, 2000

(87) PCT Pub. No.: WO00/35862

PCT Pub. Date: Jun. 22, 2000

Related U.S. Application Data

(60) Provisional application No. 60/112,972, filed on Dec. 18, 1998.

(51) Int. Cl.[7] ..................... C07C 279/28; C08G 73/00; A61L 12/14
(52) U.S. Cl. ..................... 514/609; 514/634; 514/635; 564/161; 564/188; 564/189; 564/190; 564/191; 564/201; 564/215; 564/233; 564/236
(58) Field of Search ................... 564/161, 188, 564/189, 190, 191, 201, 215, 233, 236; 514/609, 634, 635

(56) References Cited

U.S. PATENT DOCUMENTS

| 4,891,423 A | 1/1990 | Stockel |
| 4,954,636 A | 9/1990 | Merianos et al. |
| 5,149,524 A | 9/1992 | Sherba et al. |
| 5,573,726 A | 11/1996 | Dassanayake et al. |
| 5,741,886 A | 4/1998 | Stockel et al. |

FOREIGN PATENT DOCUMENTS

| CA | 2098472 | 12/1993 |
| WO | WO 97/36487 | 10/1997 |
| WO | WO 98/20738 | 5/1998 |
| WO | WO 98/20913 | 5/1998 |
| WO | WO 98/30248 | 7/1998 |

*Primary Examiner*—Brian J. Davis
(74) *Attorney, Agent, or Firm*—Gregg C. Brown

(57) ABSTRACT

Amido polybiguanides and their use as antimicrobial agents in pharmaceutical compositions are disclosed. A method of synthesis of amido polybiguanides is also disclosed. The amido polybiguanides are useful in the preservation of pharmaceutical compositions, particulary opthalmic and otic pharmaceutical compositions and compositions for treating contact lenses. The compounds are especially useful for disinfecting contact lenses.

17 Claims, No Drawings

AMIDO POLYBIGUANIDES AND THE USE THEREOF AS ANTIMICROBIAL AGENTS

This application is a 371 of U.S. 99/30207 filed Dec. 17, 1999 which claims benefit of provisional appln No. 60/112,97 Dec. 18, 1998.

BACKGROUND OF THE INVENTION

The present invention is directed to new polymeric biguanides having potent antimicrobial activity and little, if any, toxicity relative to human tissues. The amidopolybiguanides disclosed herein have many industrial applications, but are especially useful as antimicrobial preservatives in pharmaceutical compositions. The invention is particularly directed to the use of these compounds in compositions and methods for disinfecting contact lenses, and to the preservation of various types of ophthalmic and otic pharmaceutical compositions.

Contact lenses are exposed to a broad spectrum of microbes during normal wear and become soiled relatively quickly. Routine cleaning and disinfecting of the lenses are therefore required. Although the frequency of cleaning and disinfecting may vary somewhat among different types of lenses and lens care regiments, daily cleaning and disinfecting is normally required. Failure to clean and disinfect the lens properly can lead to a multitude of problems ranging from mere discomfort when the lenses are being worn to serious ocular infections. Ocular infections caused by particularly virulent microbes, such as *Pseudomonas aeruginosa*, can lead to loss of the infected eye(s) if left untreated, or if allowed to reach an advanced stage before treatment is initiated. It is therefore extremely important that patients disinfect their contact lenses in accordance with the regimen prescribed by their optometrist or ophthalmologist.

Unfortunately, patients frequently fail to follow the prescribed regimens. Many patients find regimens to be difficult to understand and/or complicated, and as a result do not comply with one or more aspects of the regimen. Other patients may have a negative experience with the regimen, such as ocular discomfort attributable to the disinfecting agent, and as a result do not routinely disinfect their lenses or otherwise stray from the prescribed regimen. In either case, the risk of ocular infections is exacerbated.

Despite the availability of various types of contact lens disinfecting systems, such as heat, hydrogen peroxide, and other chemical agents, there continues to be a need for improved systems which: 1) are simple to use, 2) have potent antimicrobial activity, and 3) are nontoxic (i.e., do not cause ocular irritation as the result of binding to the lens material). Conventional contact lens cleaners with potent antimicrobial activity also have rather high toxicity. There is, therefore, a particular need in the fields of contact lens disinfection and ophthalmic composition preservation for safe and effective chemical agents with high antimicrobial activity and low toxicity.

The use of polymeric biguanide compounds as disinfecting agents is well known. Commercially available polybiguanides are hexamethylene biguanide polymers that have end groups consisting of a cyanoguanidine group and an amino group, respectively. The widely-used polybiguanide Cosmocil CQ (polyhexamethylene biguanide or "PHMB") has strong antimicrobial activity, but rather high toxicity. A principal objective of the present invention is to provide polymeric biguanides that preserve antimicrobial activity comparable to PHMB, but are less toxic to human tissue than PHMB. As explained below, this objective has been achieved by means of a unique modification of the terminal amino groups of PHMB.

The present invention is directed to satisfaction of the above-cited needs and objectives.

SUMMARY OF THE INVENTION

The present invention is directed to polybiguanides having an amido moiety as the first terminal group and a cyanoguanidine moiety as the second terminal group. These compounds have antimicrobial activity comparable to PHMB, but are generally less toxic than PHMB. The invention is also directed to contact lens disinfecting compositions which contain the subject compounds, and to various ophthalmic compositions (e.g., pharmaceuticals, artificial tears, and comfort drops) and other types of pharmaceutical compositions that contain the compounds for purposes of preserving the compositions against microbial contamination.

The modification of the amino moiety of known polybiguanides to an amido moiety containing the substituents described herein results in good antimicrobial activity and lowered toxicity over prior art compounds. Also, the addition of specified substituents to the PHMB polymer changes its physicochemical and biochemical properties to afford a compound whose toxicity profile is lower than that of PHMB, yet maintains the antimicrobial activity of PHMB.

As discussed above, Cosmocil CQ is a widely-used, commercially available polyhexamethylene biguanide ("PHMB") disinfectant containing one terminal amino group. PHMB has strong antimicrobial activity, but rather high toxicity. A key difference between the compounds of the present invention and conventional PHMB is the modification of the terminal amino group of PHMB to form an amido group. This modification has resulted in the production of a new class of compounds having properties that are superior to those of PHMB. This invention also involves a modification of the PHMB polymer to include other substituents that change its physical, chemical, and biochemical properties to provide compounds whose toxicity profiles are lower than that of PHMB, while still maintaining the potent antimicrobial activity of PHMB.

DESCRIPTION OF THE PREFERRED EMBODIMENT

The compounds of the present invention are polybiguanides in which the first terminal group is an amido moiety and the second terminal group is a cyanoguanidine moiety. The compounds have the following formula:

RC(=O)NH—X—[NHC(=NH)NHC(=NH)NH—X—]<sub>n</sub>NHC(=NH)NHCN 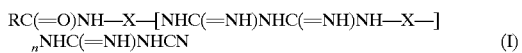 (I)

wherein:

n is a whole number in the range of 1 to 100;

X is saturated or unsaturated alkyl, cycloalkyl, alkyl substituted with cycloalkyl, aryl, or aralkyl, with the proviso that the X groups contain 1 to 40 carbon atoms ($C_1$ to $C_{40}$) and are unsubstituted or substituted with any number of N, O, S, P, B, F, Cl, Br, or I; and R is a saturated or unsaturated alkyl (C1 to C50), cycloalkyl (C3 to C50), alkyl substituted with cycloalkyl, polyethylene oxide having a molecular weight of 50 to 10,000 (M.W. 50–10,000), polypropylene oxide having a molecular weight of 50 to 10,000 (M.W. 50–10,000), any combination of the above groups, unsubstituted aralkyl, aralkyl substituted with any number of N, O, S, P, B, F, Cl, Br, or I unsubstituted aryl, or aryl substituted with any number of N, O, S, P, B, F, Cl, Br, or I.

The R substituent in compounds of formula (I) optionally include amide, urea or other covalent linking functional groups.

As utilized herein, the term "alkyl" includes straight or branched chain hydrocarbon groups. The alkyl groups may be substituted with other groups, such as halogen, hydroxyl or alkoxyl.

The preferred compounds are those wherein n is 4 to 16, X is alkyl or aralkyl, and R is polyethylene oxide (M.W. 100 to 2,000) or polyethylene oxide (M.W. 100 to 2,000) alkyl ether. The use of polyethylene oxide as the R group is preferred because this substituent has been found to be particularly effective in reducing the toxicity of biguanides. The following compounds are particularly preferred:

| Compound Number | n | X | R |
| --- | --- | --- | --- |
| 1 | 14 | $C_6H_{12}$ | $C_{13}H_{27}$ |
| 2 | 12 | $C_6H_{12}$ | polyethylene oxide (M.W. 550) succinimidyl methyl ether |
| 3 | 12 | $C_6H_{12}$ | $CH_3$ |

Compound Number 2 above is the most preferred.

The compounds of the present invention may be prepared by means of the method illustrated in Scheme 1 below:

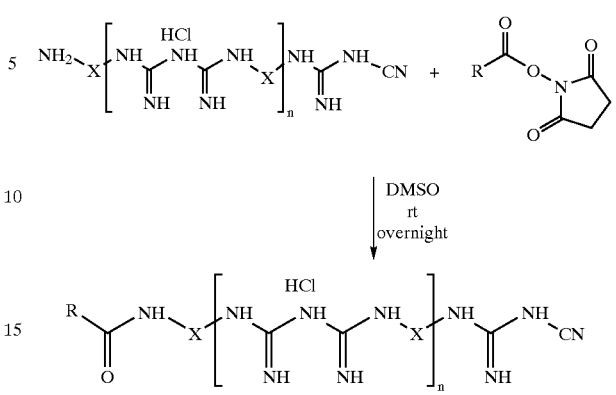

Scheme 1

In general, the synthesis of the amido biguanides of the present invention is performed by reaction of the terminal amino group of a polybiguanide with an N-hydroxysuccinimide ester of the desired substituent, R, in the presence of a sterically hindered base, preferably diisopropylethylamine, in a suitable solvent, preferrably DMSO, at ambient temperature for 8–20 hours.

The compounds of the present invention wherein R is a polyethylene oxide may be prepared by the means of the method illustrated in Scheme 2 below:

Scheme 2

Reaction Scheme for polyethylene oxide (M.W. 550) succinimidyl (Compound 4)

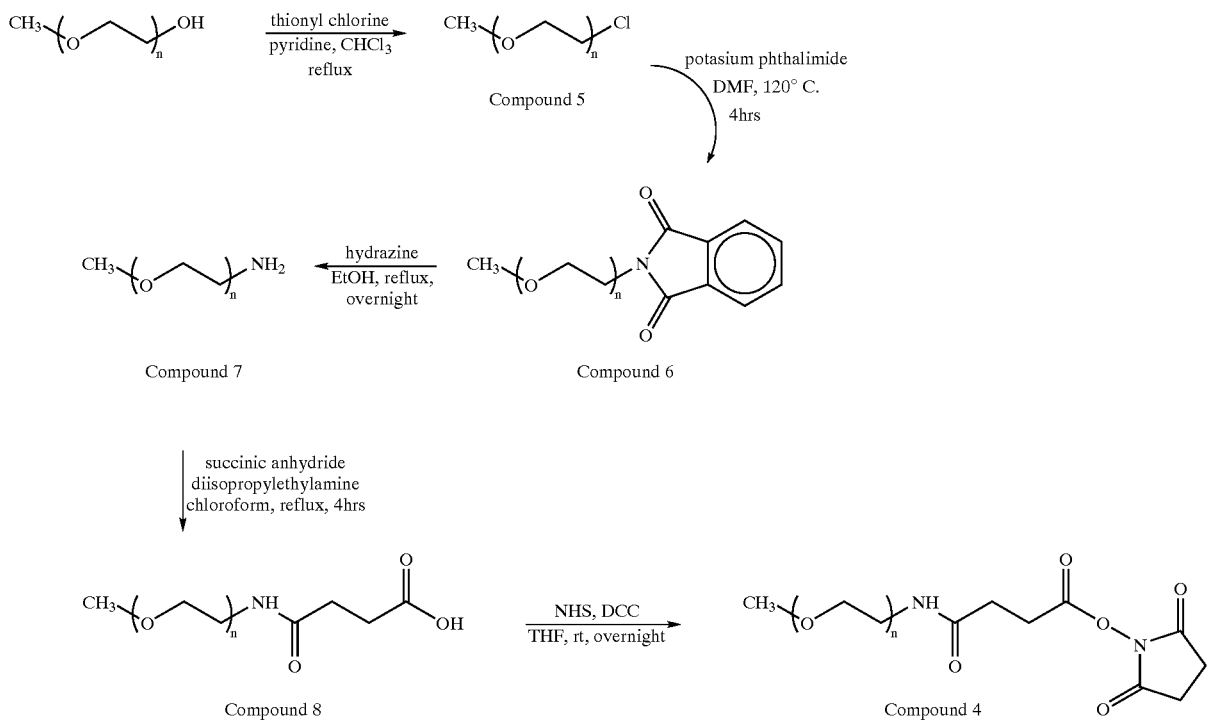

Synthesis of Compound 5

A 50 ml chloroform solution of 11.0 g (0.02 mol) poly (ethyleneglycol) (polyethyleneoxide, PEO) MW 550 monomethylether (Aldrich lot# 05022ET) and 1.6 g (0.02 mol) pyridine was added dropwise under an $N_2$ atmosphere to a 75 ml chloroform solution of 3.09 g (0.026 mol) thionyl chloride. After addition, the reaction mixture was heated to reflux (70° C.) under constant stirring for 2.5 hours. The organic layer was washed with 3×50 ml aqueous sodium chloride and sodium carbonate followed by 2×60 ml aqueous sodium chloride, dried (sodium sulfate), filtered and concentrated in vacuo to obtain 11.14 g (0.0196 mol, 98.0%) of Compound 5. The structure was confirmed with NMR by observing the change in chemical shift from a methylene adjacent to the terminal hydroxyl group ($\delta 3.69$, t, 2H) to a methylene adjacent to the terminal chloro group ($\delta 3.77$, t, 2H).

Synthesis of Compound 6

2.85 g (0.005 mol) of Compound 5 and 1.21 g (0.0065 mol) potassium phthalimide were mixed in 10 ml dimethylformamide (DMF) and heated to 120° C. under constant stirring for 4 hours. The DMF was removed in vacuo and the remaining residue was dissolved in 20 ml chloroform, filtered and concentrated in vacuo to yield 3.4 g (0.005 mol, 100%) of Compound 6. The structure was confirmed with NMR by observing the appearance of aromatic phthalimide peaks ($\delta 7.70$ and 7.85, m, 4H) and change in chemical shift from a methylene adjacent to the terminal chloro group ($\delta 3.77$, t, 2H) to a methylene adjacent to the terminal phthalimide group ($\delta 3.90$, t, 2H).

Synthesis of Compound 7

3.4 g (0.005 mol) of Compound 6 and 5 g (0.011 mol) hydrazine (35% w/w in water) were dissolved in 130 ml ethanol and heated to reflux (80° C.) overnight. The solution produced copious precipitation which was filtered after heating. The residue was dissolved in ethyl acetate and refrigerated overnight to induce precipitation of phthalhydrazide. The solution was filtered and redissolved in chloroform and refrigerated overnight. The solution was then filtered and concentrated in vacuo to yield 2.08 g (0.0038 mol, 75.6%) of Compound 7. The structure was confirmed with NMR by observing the dissappearance of phthalimide peaks and appearance of a methylene adjacent to the terminal primary amine group ($\delta 2.86$, t, 2H).

Synthesis of Compound 8

7.75 g (0.014 mol) of Compound 7, 1.75 g (0.0175 mol) succinic anhydride and 2.59 g (0.02 mol) N,N-diisopropylethylamine were dissolved in 100 ml chloroform and heated to reflux (70° C.) for four hours. The reaction mixture was then diluted to 150 ml and washed with 3×50 ml aqueous sodium chloride and 1N HCl followed by 2×50 ml aqueous sodium chloride. The solution was then dried (sodium sulfate), filtered and concentrated in vacuo to yield 7.11 g (0.011 mol, 78.2%) Compound 8. The structure was confirmed with NMR by observing the appearance of succinyl methylene groups ($\delta 2.55$ and 2.65, m, 4H) and change in chemical shift from a methylene adjacent to an amine ($\delta 2.86$, t, 2H) to a methylene adjacent to an amide ($\delta 3.44$, t, 2H).

Synthesis of Compound 4

2.85 g (0.0044 mol) of Compound 8 and 0.51 g (0.0044 mol) N-hydroxysuccinimide were dissolved in 40 ml tetrahydrofuran and stirred for 20 minutes. Then 0.91 g (0.0044 mol) 1,3-dicyclohexylcarbodiimide (DCC) were added and the reaction mixture stirred overnight. 8 drops of glacial acetic acid were added to convert the remaining DCC into DCU (dicyclohexylurea). This was monitored by IR observing the disappearance of the diimide peak (2100 cm$^{-1}$). The mixture was then concentrated in vacuo, dissolved in ethyl acetate (40 ml) and refrigerated to induce crystallization of DCU. The solution was then filtered and concentrated in vacuo to yield 3.28 g (0.0044 mol, 100%) of PEO MW 550 succinimidyl succinamide monomethyl ether. The product was confirmed with NMR by observing the appearance of the N-hydroxysuccinimide methylene groups ($\delta 2.84$, s, 4H) and change in chemical shift from succinyl methylene groups ($\delta 2.55$ and 2.65, m, 4H) to succinimidyl succinamide methylene groups ($\delta 2.99$ and 2.61, t, 4H).

The compounds of the present invention display a strong antimicrobial activity profile, as discussed above, which is similar to unmodified polyhexamethylene biguanide ("PHMB"), but exhibit significantly lower toxicity than the unmodified PHMB.

The compounds discussed herein can be used individually or in combination with other disinfectants or preservatives. The amount of each compound used will depend on the purpose of the use, e.g., disinfection of contact lenses or preservation of pharmaceutical products, and the absence or inclusion of other antimicrobial agents. The concentration determined to be necessary for the above-stated purposes can be functionally described as "an amount effective to disinfect" and "an amount effective to preserve," or "microbicidally effective amounts," or variations thereof. The concentrations used for disinfection will generally be in the range of from about 0.00001 to about 0.01% by weight based on the total weight of the composition ("wt. %"). The concentrations used for preservation will generally be in the range of from about 0.00001 to about 0.001 wt. %.

The compositions of the present inventions may be aqueous or nonaqueous, but will generally be aqueous. As will be appreciated by those skilled in the art, the compositions may contain a wide variety of ingredients, such as tonicity agents (e.g., sodium chloride or mannitol), surfactants (e.g., polyvinyl pyrrolidone and polyoxyethylene/polyoxypropylene copolymers), viscosity adjusting agents (e.g., hydroxypropyl methyl cellulose and other cellulose derivatives) and buffering agents (e.g., borates, citrates, phosphates, and carbonates). The ability of the compounds of the present invention to retain their antimicrobial activity in the presence of such agents is a significant advantage of the present invention.

The pharmaceutical compositions of the present invention will be formulated so as to be compatible with the human tissues to be treated with the compositions (e.g., tissues of the eye or ear), or the contact lenses to be treated. Formulations that meet these basic requirements are referred to herein as "pharmaceutically acceptable vehicles" for the compounds of the present invention or, in the case of compositions for treating the eye or contact lenses, "ophthalmically acceptable vehicles".

As will be appreciated by those skilled in the art, the ophthalmic compositions intended for direct application to the eye will be formulated so as to have a pH and tonicity which are compatible with the eye. This will normally require a buffer to maintain the pH of the composition at or near physiologic pH (i.e., 7.4) and may require a tonicity agent to bring the osmolality of the composition to a level at or near 280 to 320 milliosmoles per kilogram of water ("mOsm/kg"). The formulation of compositions for disinfecting and/or cleaning contact lenses will involve similar considerations as well as considerations relating to the physical effect of the compositions on contact lens materials and the potential for binding or absorption of the components of the composition by the lens.

The contact lens disinfecting compositions of the present invention will preferably be formulated as aqueous solutions, but may also be formulated as nonaqueous solutions as well as suspensions, gels, and so on. The compositions may contain a variety of tonicity agents, surfactants, viscosity adjusting agents, and buffering agents, as described above.

The above-described compositions may be used to disinfect contact lenses in accordance with processes known to those skilled in the art. More specifically, the lenses will first be removed from the eyes of the patients, and then will be immersed in the compositions for a time sufficient to disinfect the lenses. This immersion will typically be accomplished by means of soaking the lenses in a solution overnight (i.e., approximately six to eight hours). The lenses will then be rinsed and placed in the eye. Prior to immersion in the disinfecting compositions, the lenses will preferably also be cleaned and rinsed.

The compositions and methods of the present invention may be used in conjunction with various types of contact lenses, including both lenses generally classified as "hard" and lenses generally classified as "soft."

The compounds of the present invention may also be included in various types of pharmaceutical compositions as preservatives, so as to prevent microbial contamination of the compositions. The types of compositions which may be preserved by the compounds of the present invention include: ophthalmic pharmaceutical compositions, such as topical compositions used in the treatment of glaucoma, infections, allergies, or inflammation; otic pharmaceutical compositions, such as topical compositions instilled in the ear for treatment of inflammation or infection; compositions for treating contact lenses, such as disinfecting solutions, cleaning products and products for enhancing the ocular comfort of patients wearing contact lenses; other types of ophthalmic compositions, such as ocular lubricating products, artificial tears, astringents, and so on; dermatological compositions, such as anti-inflammatory compositions, as well as shampoos and other cosmetic compositions; and various other types of pharmaceutical compositions. The present invention is not limited with respect to the types of pharmaceutical compositions in which the compounds of the present invention may be utilized as preservatives.

The following examples are presented to further illustrate various aspects of the present invention.

EXAMPLE 1

The preferred amidobiguanide of the present invention, identified above as Compound Number 2, may be prepared as follows:

0.50 g (0.35 mmol) of solid Cosmocil CQ (polyhexamethylenebiguanide, average 5.5 repeat units) obtained by lyophilization of a 20% w/w aqueous solution and 0.09 g (0.70 mmol) diisopropylethylamine were dissolved in 2.5 ml dimethylsulfoxide (DMSO) and stirred at room temperature for 30 minutes under argon atmosphere. 0.39 g (0.53 mmol) of the PEO MW 550 succinimidyl succinamide monomethyl ether (Compound 4) was then added and the reaction mixture was stirred overnight. The DMSO was removed in vacuo and the remaining residue was dissolved in methanol (1.0 ml), acidified with HCl and precipitated with acetone (40 ml). The acetone was decanted off and the precipitate was dissolved in 1 ml water and precipitated with acetone (40 ml). The precipitate was then dissolved in water (5 ml) and concentrated in vacuo to remove any remaining acetone. Then the precipitate was dissolved in 5 ml water and lyophilized to obtain 0.39 g of Compound 2 (12 biguanide repeat units). NMR and elemental analysis confirm the structure. The number of repeat units was determined with NMR by comparison of integration peaks of the methylene groups adjacent to biguanide units and the polyethyleneoxide methylene groups. Elemental analysis helped confirm this finding.

Elemental Analysis calc'd for $C_{133}H_{300}N_{66}Cl_{24}O_{14}$+ $5H_2O$ (MW 3989.226): C, 40.04; H, 7.83; N, 23.17; Cl, 21.33; Found: C, 39.96; H, 7.93; N, 23.09; Cl, 20.60.

$^1$HNMR (200 MHz, $D_2O$): δ3.6 (broad peak, 48H, OC$\underline{H}_2C\underline{H}_2O$), 3.34 (s, 3H, C$\underline{H}_3O$), 3.3 (t, 48H, C$\underline{H}_2NHC(=NH)NHC(=NH)NHC\underline{H}_2$), 3.2 (t, 6H ,C$\underline{H}_2NHC(=NH)NHCN$ and C$\underline{H}_2N\overline{H}C(=O)$), 2.49 (t, 4H, $\overline{C}(=O)CH_2\underline{CH}_2C(=O)$), 1.6 (broad peak, 48H, NHC(=NH)N$\overline{H}C\underline{H}_2CH_2$), 1.37 (broad peak, 48H, NHC(=NH)NHCH$_2$CH$_2$C$\underline{H}_2$).

EXAMPLE 2

The amidobiguanide of the present invention identified above as Compound Number 1 may be prepared as follows:

0.50 g (0.35 mmol) solid Cosmocil CQ and 0.18 g N,N-diisopropylethylamine were dissolved in 3.5 ml DMSO and stirred for 45 minutes. 0.14 g N-hydroxysuccinimide ester of myristic acid (synthesized by coupling of myristic acid and N-hydroxysuccinimide in the presence of DCC) were then added and the reaction mixture stirred overnight. It was then precipitated with acetone (50 ml). The acetone was decanted off and the precipitate was dissolved in 2 ml water and precipitated with acetone (40 ml) and the acetone decanted off. This process of dissolving in water, precipitating with acetone and decanting the acetone layer was repeated two more times. The precipitate was then dissolved in 5 ml water and concentrated in vacuo to remove the remaining acetone. It was then redissolved in water (5 ml) and lyophilized to yield 0.28 g (0.079 mmol, 45%) of Compound 1 (14 biguanide units). The structure was confirmed by NMR and elemental analysis. The molecular weight was determined with NMR by comparing the integration peaks corresponding to the methylene groups adjacent to the biguanides and the terminal methyl group on the alkyl chain substituent. This was confirmed with elemental analysis.

Elemental Analysis calc'd for $C_{134}H_{295}N_{75}Cl_4O$+4.5 $H_2O$ (MW 3550.72) C, 45.33; H, 8.63; N, 29.58; Cl, 13.98; Found: C, 45.30; H, 8.76; N, 29.13; Cl, 14.23.

$^1$HNMR (200 MHz, $D_2O$): δ3.14 (broad t, 56H, C$\underline{H}_2NHC(=NH)NHC(=NH)NHC\underline{H}_2$), 2.2 (t, 2H, C$\underline{H}_2C(=O)NH$), 1.51 (broad peak, 56H, NHC(=NH)$\overline{N}HCH_2C\underline{H}_2$), 1.31 (broad peak, 56H, NHC(=NH)NHCH$_2$C$\underline{H}_2$CH$_2$), 1.21 (broad peak, 22H, CH$_3$(C$\underline{H}_2$)11), 0.8 (t, 3H, C$\underline{H}_3(C\overline{H}_2)_{11}$).

EXAMPLE 3

The amidobiguanide of the present invention identified above as Compound Number 3 may be prepared as follows:

0.50 g (0.00035 mol) solid Cosmocil CQ and 0.18 g (0.0014 mol) diisopropylethylamine were dissolved in 2.5 ml DMSO and stirred for 45 minutes. Then 0.07 g (0.00045 mol) N-hydroxysuccinimide ester of acetic acid were added and the reaction mixture stirred overnight. The mixture was then precipitated with acetone and the acetone layer was decanted off. Then the process of dissolving the precipitate in 1 ml water, precipitating with acetone and then decanting off the acetone was repeated three times. The precipitate was then dissolved in water, concentrated in vacuo, redissolved in water and lyophilized to yield 0.14 g (0.000049 mol, 25%) of compound 3 (12 biguanide repeat units). The structure was confirmed by NMR and elemental analysis. The number of repeat units was determined with NMR by comparing the intergration peaks of the terminal methyl group with the methylene groups adjacent to the biguanide.

Elemental analysis calc'd for $C_{106}H_{235}N_{65}Cl_{12}O$ (MW 2861.92): C, 44.49; H, 8.28; N, 31.81; Cl, 14.87 Found C, 44.96; H, 8.34; N, 31.17; Cl, 14.60.

$^1$HNMR (200 MHz, $D_2O$): δ3.15 (broad t, 48H, $CH_2NHC$(=NH)NHC(=NH)NH$\underline{CH_2}$), 1.93 (s, 3H, $CH_3C$(=O)NH), 1.52 (broad peak, 48H, $\overline{NHC}$(=NH)NHC$\overline{H_2}CH_2$), 1.31 (broad peak, 48 H, NHC(=NH)NHCH$_2$CH$_2$C$\underline{H_2}$).

EXAMPLE 4

The following formulation is provided to further illustrate the compositions of the present invention, particularly compositions utilized to disinfect contact lenses.

| Ingredient | Amount (wt. %) |
|---|---|
| Compound | 0.00001 to 0.01 |
| Boric Acid | 0.58 |
| Sodium Borate | 0.18 |
| Sodium Chloride | 0.49 |
| Disodium Edetate | 0.05 |
| NaOH/HCl | q.s. pH 7.0 |

In this formulation, the term "Compound" refers to any of the compounds of the present invention, particularly those of formula (I) above.

EXAMPLE 5

The antimicrobial activity of the compounds of the present invention is demonstrated by the microbiological data provided in the table below. Three compounds of the present invention (i.e., Compound No. 1, Compound No. 2 and Compound No. 3) were tested at concentrations of 0.0005 wt. %. The compounds were tested using either water or the formulation of Example 4 as the vehicle for the compounds. (The formulation of Example 4 is referred to in the table below as "FID 84509".) A description of the test procedures is provided following the table.

spectrophotometrically to a concentration of approximately $1.0\times10^8$ colony forming units mL (CFU/mL).

The test compounds were prepared at target concentrations in selected vehicles. Ten mL of test solution was inoculated with 0.1 mL of the appropriate microbial suspension so that the test solution contained approximately $1.0\times10^6$ CFU/mL. The tubes were thoroughly mixed and kept at room temperature during the test.

At six and 24 hours after test solution inoculation, a 1.0 mL aliquot from each test sample and for each challenge organism was transferred to 9.0 mL Dey Engley Neutralizing Broth blanks. The samples were serially diluted in the neutralizing broth and pour plates were prepared from appropriate dilutions with SCDA containing neutralizers. Petri plates were incubated for 48–72 hours and the number of survivors visible as discrete colony forming units were determined according to standard microbiological methods.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A compound of the following formula:

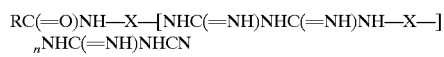
$$_nNHC(=NH)NHCN$$

wherein:

n is a whole number in the range of 1 to 100;

X is saturated or unsaturated alkyl, cycloalkyl, alkyl substituted with cycloalkyl, aryl, or aralkyl, with the proviso that the X groups contain 1 to 40 carbon atoms ($C_1$ to $C_{40}$) and are unsubstituted or substituted with any number of N, O, S, P, B, F, Cl, Br, or I; and R is a saturated or unsaturated alkyl (C1 to C50), cycloalkyl (C3 to C50), alkyl substituted with cycloalkyl, polyethylene oxide having a molecular weight of 50 to 10,000 (M.W. 50–10,000), polypropylene oxide having a molecular weight of 50 to 10,000

|  |  | Log$_{10}$ Reduction of Survivors |  |  |  |  |  |
|---|---|---|---|---|---|---|---|
|  |  |  | Water |  |  | FID 84509 |  |
| Microorganism | Time (hrs) | Cmpd. 1 | Cmpd. 2 | Cmpd. 3 | Cmpd. 1 | Cmpd. 2 | Cmpd. 3 |
| C. albicans | 6 | 1.9 | 2.3 | 3.1 | 2.2 | 1.7 | 2.3 |
|  | 24 | 0.9 | 1.0 | 2.9 | 2.3 | 1.6 | 2.4 |
| S. marcescens | 6 | <u>6.2</u> | <u>6.2</u> | <u>6.1</u> | <u>6.2</u> | 5.5 | 4.4 |
|  | 24 | <u>6.2</u> | <u>6.2</u> | <u>6.1</u> | <u>6.2</u> | <u>6.2</u> | <u>6.1</u> |
| S. aureus | 6 | <u>6.2</u> | 5.5 | 6.0 | <u>6.2</u> | 5.0 | <u>3.9</u> |
|  | 24 | 5.5 | <u>6.2</u> | 6.0 | <u>6.2</u> | 5.5 | 4.0 |

$^a$Underlined number indicates no survivors (<10 CFU/mL) recovered.

The bacteria *Serratia marcescens* ATCC 13880 and *Staphylococcus aureus* ATCC 6538 were cultured on soybean casein digest agar (SCDA) slants. The yeast *Candida albicans* ATCC 10231 was cultured on Sabouraud Dextrose Agar slants. Surface growth of the three microorganisms was harvested with phosphate buffered saline containing Polysorbate 80. The microbial suspensions were adjusted (M.W. 50–10,000), any combination of the above groups, unsubstituted aralkyl, aralkyl substituted with any number of N, O, S, P, B, F, Cl, Br, or I, unsubstituted aryl, or aryl substituted with any number of N, O, S, P, B, F, Cl, Br, or I, optionally containing one or more amide or urea covalent linking functional groups.

2. The compound of claim 1, wherein R is polyethylene oxide having a molecular weight of 50 to 10,000.

3. A pharmaceutical composition comprising a microbicidally effective amount of the compound of claim 1.

4. An ophthalmic composition for disinfecting contact lenses, comprising:

a compound of the following formula in an amount effective to disinfect contact lenses:

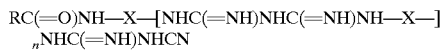
$_n$NHC(=NH)NHCN wherein:

n is a whole number in the range of 1 to 100;

X is saturated or unsaturated alkyl, cycloalkyl, alkyl substituted with cycloalkyl, aryl, or aralkyl, with the proviso that the X groups contain 1 to 40 carbon atoms ($C_1$ to $C_{40}$) and are unsubstituted or substituted with any number of N, O, S, P, B, F, Cl, Br, or I; and R is a saturated or unsaturated alkyl (C1 to C50), cycloalkyl (C3 to C50), alkyl substituted with cycloalkyl, polyethylene oxide having a molecular weight of 50 to 10,000, polypropylene oxide having a molecular weight of 50 to 10,000, any combination of the above groups, unsubstituted aralkyl, aralkyl substituted with any number of N, O, S, P, B, F, Cl, Br, or I, unsubstituted aryl, or aryl substituted with any number of N, O, S, P, B, F, Cl, Br, or I, optionally containing one or more amide, or urea covalent linking functional groups; and an ophthalmically acceptable vehicle for said compound.

5. A method of disinfecting a contact lens which comprises immersing the lens in the composition of claim 4 for a time sufficient to disinfect the lens.

6. A method of preserving a pharmaceutical composition from microbial contamination which comprises including in the composition a preservative effective amount of a compound of the following formula:

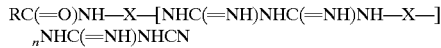
$_n$NHC(=NH)NHCN wherein:

n is a whole number in the range of 1 to 100;

X is saturated or unsaturated alkyl, cycloalkyl, alkyl substituted with cycloalkyl, aryl, or aralkyl, with the proviso that the X groups contain 1 to 40 carbon atoms ($C_{1\ to\ C40}$) and are unsubstituted or substituted with any number of N, O, S, P, B, F, Cl, Br, or I; and R is a saturated or unsaturated alkyl (C1 to C50), cycloalkyl (C3 to C50), alkyl substituted with cycloalkyl, polyethylene oxide having a molecular weight of 50 to 10,000 (M.W. 50–10,000), polypropylene oxide having a molecular weight of 50 to 10,000 (M.W. 50–10,000), any combination of the above groups, unsubstituted aralkyl, aralkyl substituted with any number of N, O, S, P, B, F, Cl, Br, or I, unsubstituted aryl, or aryl substituted with any number of N, O, S, P, B, F, Cl, Br, or I, optionally including one or more amide or urea covalent linking functional groups.

7. A method according to claim 6, wherein the composition is an ophthalmic pharmaceutical composition.

8. A method according to claim 6, wherein the composition is an otic pharmaceutical composition.

9. The compound of claim 1, wherein n is 4 to 16, x is alkyl or aralkyl and R is polyethylene oxide (M.W. 100 to 2,000) or polyethylene oxide (M.W. 100 to 2,000) alkylether.

10. The pharmaceutical composition of claim 3, wherein n is 4 to 16, x is alkyl or aralkyl and R is polyethylene oxide (M.W. 100 to 2,000) or polyethylene oxide (M.W. 100 to 2,000) alkylether.

11. The ophthalmic composition of claim 4, wherein n is 4 to 16, x is alkyl or aralkyl and R is polyethylene oxide (M.W. 100 to 2,000) or polyethylene oxide (M.W. 100 to 2,000) alkylether.

12. The method of claim 5, wherein n is 4 to 16, x is alkyl or aralkyl and R is polyethylene oxide (M.W. 100 to 2,000) or polyethylene oxide (M.W. 100 to 2,000) alkylether.

13. The method of claim 6, wherein n is 4 to 16, x is alkyl or aralkyl and R is polyethylene oxide (M.W. 100 to 2,000) or polyethylene oxide (M.W. 100 to 2,000) alkylether.

14. The method of claim 7, wherein n is 4 to 16, x is alkyl or aralkyl and R is polyethylene oxide (M.W. 100 to 2,000) or polyethylene oxide (M.W. 100 to 2,000) alkylether.

15. The method of claim 8, wherein n is 4 to 16, x is alkyl or aralkyl and R is polyethylene oxide (M.W. 100 to 2,000) or polyethylene oxide (M.W. 100 to 2,000) alkylether.

16. A compound according to claim 1, wherein R is polyethylene oxide (M.W. 550) succinimidyl methyl ether.

17. A compound according to claim 16, wherein n is 12 and X is $C_6H_2$.

* * * * *